Figure 1:
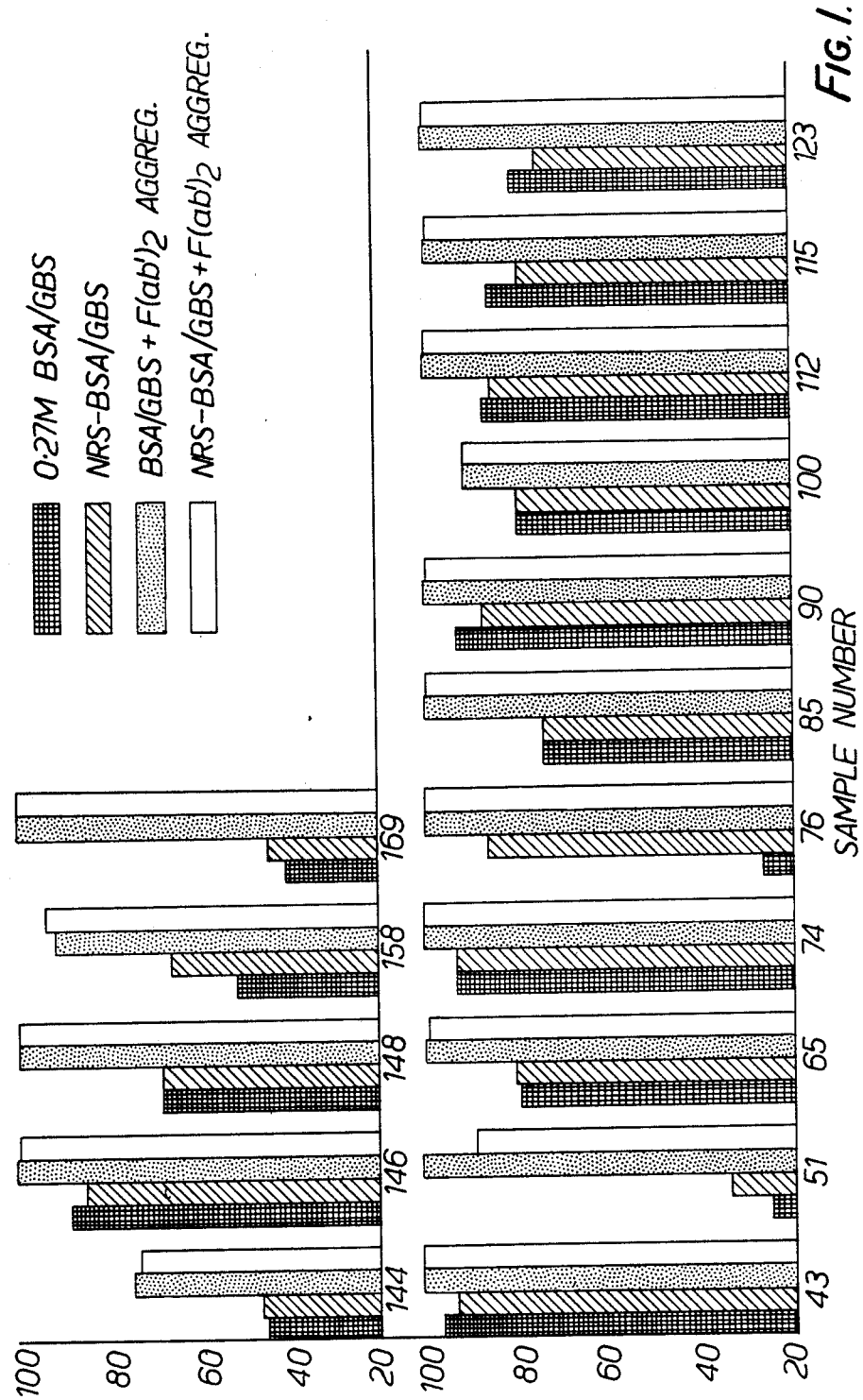

United States Patent [19]

Collet-Cassart et al.

[11] Patent Number: 4,946,796

[45] Date of Patent: Aug. 7, 1990

[54] METHOD OF IMMUNOASSAY

[75] Inventors: Daniel Collet-Cassart, Kraainem; Carl-Gustav M. Magnusson; Pierre L. Masson, both of Brussels, all of Belgium

[73] Assignee: International Institute of Cellular & Molecular Pathology, Brussels, Belgium

[21] Appl. No.: 34,246

[22] Filed: Apr. 6, 1987

Related U.S. Application Data

[63] Continuation of Ser. No. 770,045, Aug. 2, 1985, abandoned, which is a continuation of Ser. No. 452,180, Dec. 22, 1982, abandoned.

[51] Int. Cl.$^5$ ............... G01N 33/563; G01N 33/546; G01N 33/53; G01N 33/566
[52] U.S. Cl. .................... 436/512; 436/501; 436/513; 436/518; 436/534; 436/547; 436/825
[58] Field of Search ............... 435/4, 7, 69, 814, 815; 436/512, 513, 518, 531, 533, 534, 529, 538, 539, 541, 540, 501, 547, 825

[56] References Cited

PUBLICATIONS

Collet-Cassart, D. et al, *Clin. Chem.,* vol. 27, No. 1, pp. 64–67 (1981).
Hashida, S. et al, CA103 (17):13987b (1985).

*Primary Examiner*—Esther M. Kepplinger
*Assistant Examiner*—Toni R. Scheiner
*Attorney, Agent, or Firm*—Jeffrey M. Greenman

[57] ABSTRACT

A biological fluid from a first animal species (e.g. human serum) is assayed for an immunogen therein by mixing with the fluid (Ig-minus-Fc) fragments of an immunoglobulin from a second animal species (e.g. rabbit), the immunoglobulin being immunospecific to the immunogen or another component of the mixture whereby the immunogen can be determined. Interference can occur from reaction between first animal species antibodies and the said fragments, and in the method of the invention this interference is avoided or overcome, preferably by also including in the mixture different (Ig-minus-Fc) immunoglobulin fragments from the second animal species which react with said antibodies but not with said immunogen. These different fragments are preferably aggregated. The method of the invention is particularly applicable to particle agglutination assays.

8 Claims, 3 Drawing Sheets

METHOD OF IMMUNOASSAY

CROSS REFERENCE TO RELATED APPLICATION

This application is a continuation of application Ser. No. 06/770,045 filed Aug. 24, 1985, now abandoned, which was a continuation of application Ser. No. 06/452,180 filed Dec. 22, 1982, now abandoned.

This invention relates to a method of immunoassay, more particularly to a method of immunoassay in which there are utilised fragments of immunoglobulins.

In our U.K. patent specification no. 2013211A, we have described a method of immunoassay which comprises reacting an antigen (which term includes haptens) in a fluid with the F(ab')$_2$ fragments of an immunoglobulin which is specific to said antigen, the reaction being effected in the substantial absence of the (whole) immunoglobulin and F(c) fragments thereof. Whilst reference should be made to the above specification for full details, the main purpose and advantage of using the F(ab')$_2$ fragments instead of the whole immunoglobulin (and in the absence of F(c) fragments) are to avoid interference in the assay from rheumatoid factor (RF) and C1q (a component of complement) which can both occur in human sera.

The method above described is useful inter alia in particle agglutination assays, and in such assays particularly of human sera, other types of interference can also occur. For example, non-specific particle agglutination can be caused by the presence of serum proteins generally, and we have described a way of overcoming this by enzymic digestion (see our European patent specification no. 51985). The use of enzymic digestion to avoid general serum protein interference is generally practicable only when the antigen under assay (or a defined fragment of that antigen - European specification no. 51985) is stable to the enzyme, e.g. with antigens such as thyroxine or progesterone where pepsin is the enzyme. Another way of reducing or avoiding serum protein interference involves the use of chaotropic agents (see our European patent specification no. 38181), and whilst this technique has broad applicability, it is limited to relatively weak agglutinating forces which, however, can reduce the precision of the assay.

As is well known, it is common practice in the immunoassay art to obtain antisera (against any particular antigen to be assayed) from animal sources, the commonest sources being rabbits, goats and sheep. In the assay of antigens in human sera, using antibodies from animal sources, interferences can arise occasionally because certain human patients have antibodies to the animal immunoglobulins. It is known to deal with this problem by adding to the human sera a large quantity of the animal immunoglobulin (but not that which is specific to the antigen under assay) and thereby to cause any antibodies in the human serum which are reactive with the animal immunoglobulin to react and so subsequently be unavailable to interfere in the assay.

We have found that even when the above-described precautions are taken to avoid interference in particle agglutination assays, the results obtained for as many as 1 to 2% of sera in certain assays may be very significantly inaccurate. As a result of extensive investigations, we have found that this inaccuracy is due to a hitherto unknown and totally unexpected fact, namely that some human sera can contain antibodies which are unreactive to whole (non-human) animal immunoglobulin but yet reactive towards F(ab')$_2$ fragments thereof. This is most surprising since whilst it has been known in the art that, within any particular species, antibodies may exist which will react with F(ab')$_2$ fragments but not with whole immunoglobulin, it has always been accepted that this effect can only occur within a single species and not as between two quite t species (see, for example, M. Waller, American Journal of Medicine, Vol. 54, page 731, June 1973).

Furthermore, we have established that this effect can give rise to inaccuracies in immunoassays in which F(ab')$_2$ fragments are used which have been derived from an animal source of a different species from the source of the biological fluid (e.g. human serum) under assay.

In addition, it also appears that when human serum contains antibodies which react with non-human (Fab')$_2$ fragments, these antibodies may also react (albeit only weakly) with other (non-human) "Fab" fragments of immunoglobulins. Thus, it can be seen that, in general, immunoassays utilising (Ig-minus-Fc) fragments (Ig means immunoglobulin) of an antibody can suffer interference because of the possibility of reaction therewith by antibodies thereto, of a different species. This source of possible interference in immunoassays utilising (Ig-minus-Fc) antibody fragments has been hitherto totally unsuspected because, as described above, cross-species interactions of this sort have been thought never to occur.

Broadly, therefore, the present invention provides a method of immunoassay of an immunogen in a biological fluid from a first animal species, in which method there is used as a reactant (Ig-minus-Fc) fragments (hereinafter called "specific fragments") of an immunoglobulin from a second animal species, in the absence of the whole immunoglobulin and of the F(c) fragments thereof, the said immunoglobulin being immunologically specific to a component of the assay reaction mixture, and wherein the method includes the step of avoiding or reducing interference in the assay from reaction between the said fragments and any first species antibodies thereto present in the said biological fluid.

In the method of the invention, the "specific fragments" used are derived from an immunoglobulin (usually but not necessarily IgG) which is immunologically specific to a component of the reaction mixture. Thus, for example, the fragments may be immunologically specific to the immunogen under assay, so that they react directly therewith. Alternatively, they may be specific to another component of the reaction mixture which, for example, is present or generated in an amount dependent on the immunogen, so that the immunogen is detected or quantified indirectly rather than by direct reaction with the fragments.

The preferred (Ig-minus-Fc) fragments are F(ab')$_2$ fragments of IgG, but as is known in the art other fragments such as Fab' or Fab-fragments can sometimes be used (as can fragments from immunoglobulins other than IgG), in immunoassays in place of whole immunoglobulin.

In the method of the present invention, interference caused by reaction between the "specific fragments" and any first species antibodies thereto (which will be essentially IgM) in the sample to be assayed is avoided or at least substantially reduced. There are several ways in which this can be accomplished. The presently preferred procedure is to treat the sample under assay with one or more substances which selectively inactivate the interfering first species antibodies, without themselves causing any interference in the assay. According to a highly preferred feature of the invention, use is made for this purpose of certain (Ig-minus-Fc) fragments, preferably F(ab')$_2$ fragments termed herein "non-specific fragments". "Non-specific fragments" are to be differentiated from "specific fragments" as follows:

"specific fragments" are second species (Ig-minus-Fc) fragments which are capable of reacting both with the immunogen (or other component of the reaction mixture) under assay, and with any first species antibodies thereto (whose presence would give rise to interference);

"non-specific fragments" are second species (Ig-minus-Fc) fragments which are not capable of reacting with the immunogen, but are capable of reacting with the said first species antibodies.

Thus, by treating the sample to be assayed with "non-specific fragments", first species antibodies therein directed against second species fragments will become bound to the "non-specific fragments" and so be unable to interfere in the assay by reaction with "specific fragments".

As is known, F(ab')$_2$ fragments are divalent immunoglobulin fragments. However, whilst some of the first species antibodies thereto will be divalent (i.e. IgG), a proportion will certainly be multivalent (IgM). In order to improve the efficiency of binding between the "non-specific fragments" and the first species antibodies thereto, we prefer to use aggregated "non-specific fragments", since the latter are multivalent and the binding efficiency of IgM antibodies thereto is greater.

The "non-specific fragments" may be aggregated by heat or chemically and in both cases are soluble in buffers. Heat aggregates are not stable at high dilution over prolonged periods of time and we therefore prefer to use chemically aggregated "non-specific fragments". The preparation of both heat- and chemically-aggregated fragments is known in the art and described in the literature.

Whilst the use of aggregated non-specific fragments is highly preferred, it is also possible instead to couple the non-specific fragments to, for example, a solid insoluble support or to a soluble substance such as a protein. Suitable solid supports include, for example, polystyrene, Sepharose or polyacrylamide.

When the method of the invention is conducted using non-specific fragments, it is preferred that such fragments be obtained from the same animal source as the "specific fragments". For example, non-specific fragments would preferably be obtained from a non-immunised rabbit, and then the rabbit would be immunised to provide specific fragments. In practice, however, fragments are best obtained by pooling blood samples from a collection of, say, rabbits, both before and after immunisation. This procedure avoids any problem which might arise if the non-specific fragments from any particular individual animal were less reactive (than the norm) towards the first species (usually human) antibodies.

Whilst the use of "non-specific fragments" is, as described, highly preferred in the method of the invention, the invention is not limited to the use of such substances. Other reagents or techniques may be used to remove or reduce the interference arising from reaction of the first species antibodies with the "specific fragments", including other substances or techniques by which the said antibodies can be selectively inactivated or removed from the sample, e.g. by use of chaotropic agents, enzymic digestion or by reduction of disulfide bridges to destroy IgM anti-F(ab')$_2$ antibodies.

The precise manner in which the preferred "non-specific fragments" are used in the method of the invention can vary. For example, aggregated "non-specific fragments" can simply be mixed with the biological fluid and may remain therein during the assay or be removed. An alternative, though less preferable, procedure is to pre-treat the biological fluid, before assay, by contacting it with the aggregated "non-specific fragments" or with, for example, "non-specific fragments" immobilised on a solid phase support. For example, a column of material may be used.

Whilst the method of the invention is particularly useful in particle agglutination assays it may also be used in other immunoassays in which (Ig-minus-Fc) fragments are employed as reactants and reference may be made here, by way, of example, to our U.K. patent specifications nos. 2013211A, 2045431A, and U.S. Pat. No. 4184849. The method, in either case, may be effected manually or on an automated continuous or semi-continuous basis.

In the preferred particle agglutination assays, an antigen is assayed by mixing it with finely divided latex particles bearing the "specific fragments". The antigen causes agglutination of the particles to an extent dependent on the amount of antigen present. By counting the number of particles remaining unagglutinated, a measure of the amount of antigen present can be obtained. This general procedure, which can be modified in a variety of ways, is well known in the art and further description thereof is unnecessary.

The method of the invention (whether applied to particle agglutination assays or other assays) is very widely applicable in the assay of immunogens in general. It is particularly useful in the assay of alphafetoprotein in human serum, ferritin, human placental lactogen, thyroxin-binding globulin and in many assays in which the use of strong chaotropic agents would lead to degradation of the antigens. Such substances can be the stimulating hormones (thyroid stimulating and follicle stimulating hormones, etc.) enzymes (acid phosphatase) and certain large viral antigens.

In order that the invention be more fully understood, the following experimental results are given by way of illustration.

1. Aggregated rabbit F(ab')$_2$
   (a) Rabbit F(ab')$_2$ fragments were obtained as described in our U.K. patent specification no. 2013211A.
   (b) Heat-aggregated fragments may be prepared by simple heating to 63° C. for 30 minutes.
   (c) Chemically aggregated fragments were prepared as follows To a solution containing 5–10 mg/ml of F(ab')$_2$ (rabbit) in a bicarbonate buffer (0.1N NaHCO$_3$, pH 8.8), a 25% solution of glutaraldehyde was added to a final reaction concentration of 0.5%. The mixture was incubated with agitation for 30 minutes at room temperature (approx. 25° C.) and the reaction was then stopped by the addition of an equal volume of 2.5% ethanolamine, pH 8.5. The mixture was then dialysed exhaustively against glycine-buffered saline (GBS) and the resulting aggregated F(ab')$_2$ was diluted in a glycine-buffered saline containing 10% pooled normal rabbit serum at concentrations of 0.1 mg/ml of aggregated F(ab')$_2$. Serum for assay was diluted 1:10 in the above mixture.

2. To show that, in assays using F(ab')$_2$ fragments, interference arises from interaction between the second species (in this case rabbi fragments and first species (in this case human) antibodies thereto, we made the following tests using an assay developed for the determination of alpha-fetoprotein. Rabbit anti-human alpha-fetoprotein immunoglobulins were treated to produce the F(ab')$_2$ fragments thereof ("specific fragments"). We first screened about 200 sera to identify those which would agglutinate latex particles coated with "non-specific fragments", in the absence of alpha-fetoprotein. For this purpose, we prepared F(ab')$_2$ fragments from non-immunized rabbits (i.e. "non-specific fragments") and bound them covalently to latex in the same way and in the same quantity as in normal preparations of latex using sera from immunized rabbits. According to the prior art teachings, such latex would not be expected to agglutinate in serum, even in the presence of RF or C1q. The results are shown in FIG. 1 which shows four particle counts for each of sixteen sera, these sixteen sera being those which showed interference. In the Figure, each sample is numbered, and for each sample the particle count was determined as follows:

Left-hand column: the count when latex particles bearing "non-specific fragments" are mixed with the serum in 0.27M BSA/GBS (BSA means bovine serum albumin).

Second column (from left): the count when normal rabbit serum is also included.

Third column (from left): the count when latex particles bearing "non-specific fragments" are mixed with the serum (in 0.27M BSA/GBS), and aggregated "non-specific fragments" are also added.

Right hand column: as for third column but also with normal rabbit serum included.

It should be understood that the higher the particle count, the lower is the interference since it is the unagglutinated particles which are counted.

Referring to FIG. 1, the sixteen sera showed varying degrees of agglutination (left hand columns) from very severe (No. 51,76) to slight (No. 43,146). The second columns show that the addition of normal rabbit sera (10% of sample) significantly reduced the interference of only one (No. 76), while the third columns show that the addition of rabbit F(ab')$_2$ aggregates (0.1 mg/ml) substantially removed the interference from all but two (No. 144,100). The addition of normal rabbit serum (right-hand columns) did not totally remove the interference in any serum.

It can be seen, therefore, that latex coated with "non-specific fragments" is agglutinated (in certain sera) but that this agglutination can be prevented by including aggregated "non-specific fragments" in the mixture. The effect of additions of normal rabbit serum was slight, indicating that the agglutination was in fact being caused by antibodies (in the human serum) which reated with rabbit F(ab')$_2$ fragments but not with rabbit whole immunoglobulin.

To check whether the immunoglobulins from other species would also be effective in removing this interference, we tried goat F(ab')$_2$, human F(ab')$_2$ aggregated and unaggregated, human aggregated IgG and rabbit aggregated IgG Neither human nor rabbit IgG, aggregated or unaggregated, nor goat F(ab')$_2$ removed interference. While human F(ab')$_2$ was effective with some sera, no effect was noted on others.

3. To determine whether the interference was due to IgG or IgM antibody, 3 of the above sera showing strong interference with non-specific fragments, were treated with dithiothreitol (DTT) 0.3% w/v at 37° C. for 10 minutes to destroy IgM. Two of the three sera lost their interference when goat anti-human IgM sera was added to the same three sera exhibiting interference. The same two sera which lost their interference after DTT treatment lost their interference in this experiment. The interferences were therefore clearly IgG and IgM.

4. A further experiment was performed to determine the efficiency of unaggregated F(ab')$_2$ in comparison with aggregated. Six sera exhibiting agglutination with non-specific fragments were treated with F(ab')$_2$ aggregated by heat, chemically and by unaggregated non-specific fragments. The unaggregated fragments reduced the interference significantly but not completely at concentrations 2-3 times higher than above mentioned. Chemically aggregated non-specific fragments were marginally more efficient than heat aggregated, and because of their better stability are therefore preferred.

5. To further illustrate the method of the invention in particle agglutination assays, three series of about 40 sera were analysed for alpha-fetoprotein. The results are in Table I:
  1. Column 1 by RIA (radioimmunoassay) using the "Dainabot AFP Kit" (Abbott Laboratories).
  2. Column 2 by PACIA (particle counting immunoassay) without the aggregated F(ab')$_2$ but with glycine buffered saline containing normal rabbit serum (GBS/NRS).
  3. Column 3 by PACIA with F(ab')$_2$ aggregates in GBS/NRS.
  4. Column 4 using latex with non-immunised rabbit F(ab')$_2$ to show self-agglutination interference. (Results are expressed in % of response curve depression.) Buffer is the same as in (2) above.
  5. Column 5, same as (4) above but now with F(ab')$_2$ in buffer.

In only 2 cases did the F(ab')$_2$ aggregates fail to remove completely all interferences (210581-24, -27). Clinically, the remaining interference is not significant.

Figure 2:
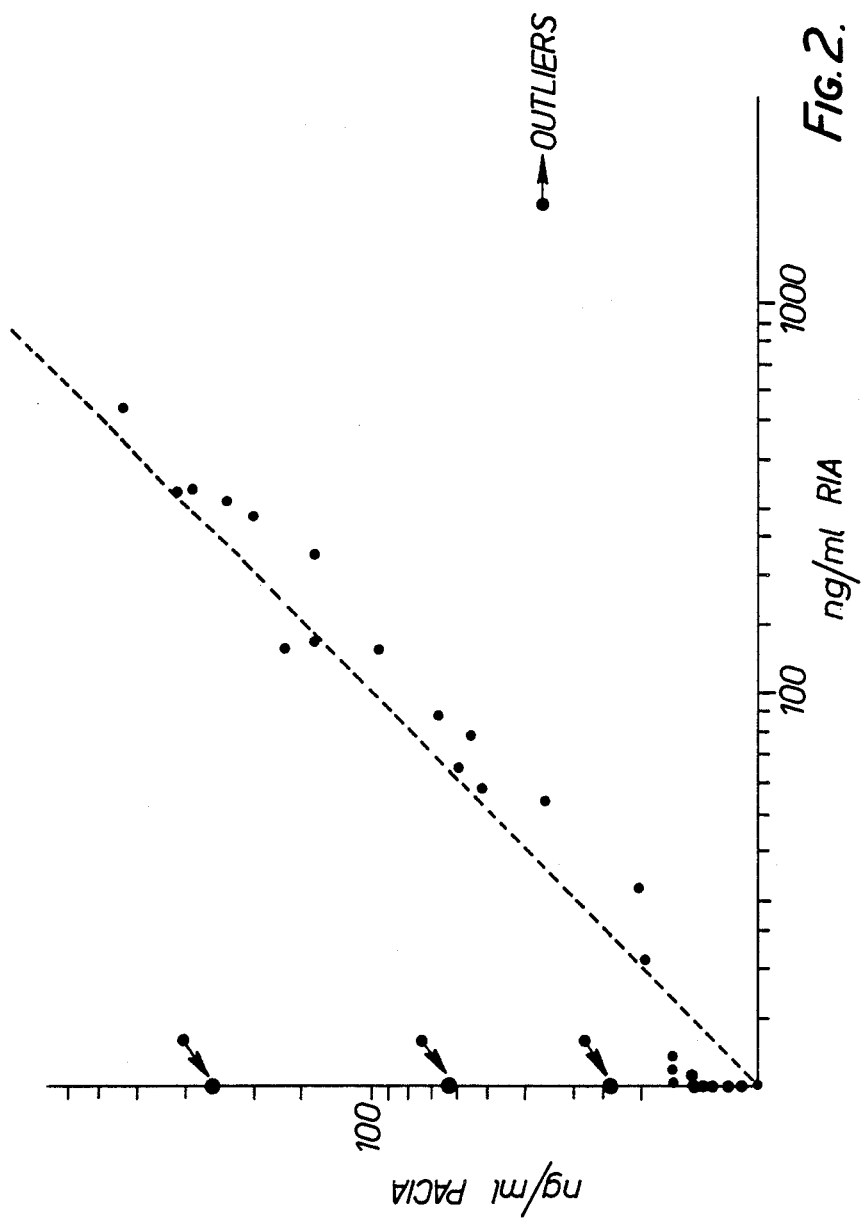
Figure 3:
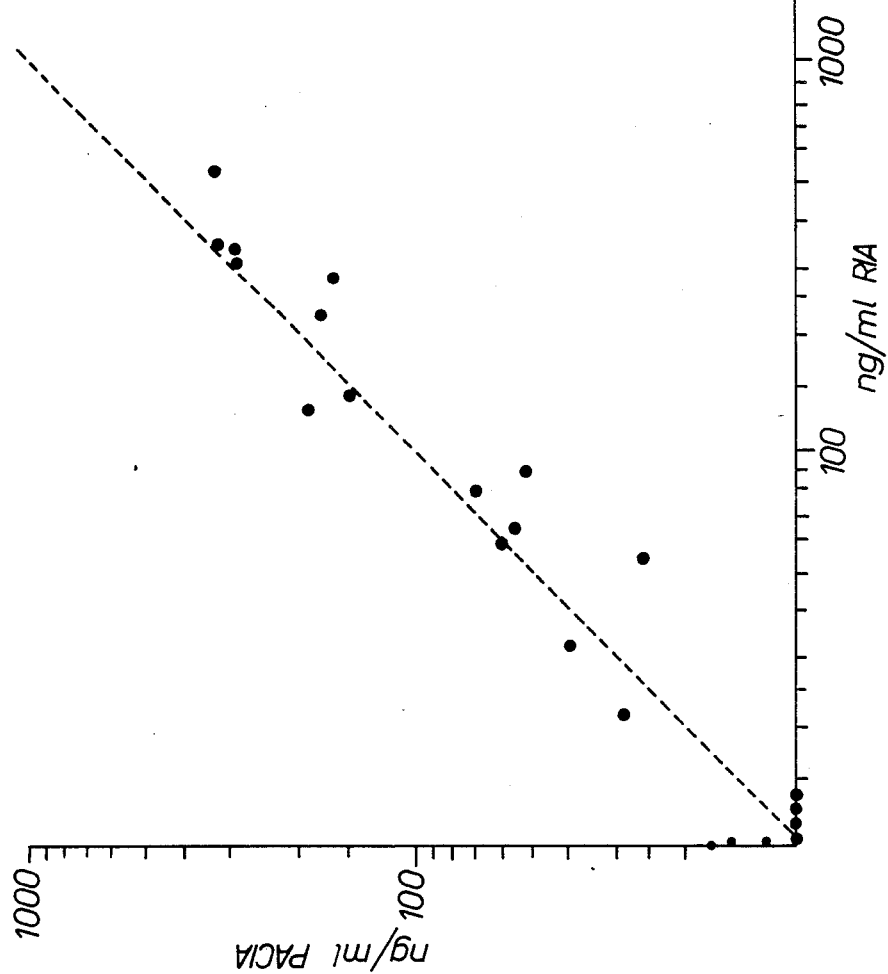

FIG. 2 shows the scattergram of positive sera (PACIA vs. RIA) not using aggregated F(ab')$_2$ as compared to the scattergram (FIG. 3) for the same sera using aggregated F(ab')$_2$ The correlation and slope are obviously improved.

6. To further illustrate the invention 99 sera from women in the 16th plus week of pregnancy were analysed for alpha-fetoprotein and the results are shown in Table 2, in which:

column A is sample no.
  column B is week of pregnancy
  column C is alpha-fetoprotein measured by radioimmunoassay
  column F is the means result of the two particle agglutination assays (D,E) not according to the invention
  column I is the mean result of the two particle agglutination assays (G,H) carried out as in D and E, but also including aggregated F(ab')$_2$ fragments in accordance with the invention.

The improvement using F(ab')₂ aggregates in accordance with the invention is shown by the following statistics:

| | |
|---|---|
| Mean value by RIA | 34.6 mg/ml |
| Mean value by PACIA | 34.6 mg/ml |
| using F(ab')₂ aggregates Mean value by PACIA using NRS but no F(ab')₂ aggregates | 45.6 mg/ml |

TABLE 1

| SERUM NO. | 1 RIA | 2 PACIA | 3 PACIA + AGG. + F(AB')₂ | 4 INTERF. | 5 INTERF. |
|---|---|---|---|---|---|
| 180581- 1 | <10 | <10 | <10 | — | — |
| 3 | 282 | 205 | 160 | — | — |
| 4 | <10 | 10 | <10 | — | — |
| 5 | <10 | <10 | <10 | — | — |
| 6 | <10 | <10 | <10 | — | — |
| 7 | 54 | 36 | 25 | — | — |
| 8 | 13.8 | <10 | <10 | — | — |
| 9 | <10 | <10 | <10 | — | — |
| 10 | <10 | <10 | <10 | — | — |
| 11 | 130 | 97 | 68 | — | — |
| 12 | <10 | <10 | <10 | — | — |
| 13 | <10 | <10 | <10 | — | — |
| 14 | <10 | <10 | <10 | — | — |
| 15 | <10 | <10 | <10 | — | — |
| 16 | 11.9 | 17 | 10 | — | — |
| 17 | <10 | <10 | <10 | — | — |
| 18 | <10 | 14 | 10 | — | — |
| 19 | <10 | <10 | <10 | — | — |
| 21 | <10 | <10 | <10 | — | — |
| 22 | <10 | <10 | <10 | — | — |
| 23 | <10 | <10 | <10 | — | — |
| 24 | <10 | <10 | <10 | — | — |
| 25 | <10 | <10 | <10 | — | — |
| 26 | <10 | <10 | <10 | — | — |
| 27 | <10 | <10 | <10 | — | — |
| 28 | <10 | <10 | <10 | — | — |
| 29 | <10 | <10 | <10 | — | — |
| 30 | <10 | <10 | <10 | — | — |
| 31 | <10 | <10 | <10 | — | — |
| 32 | <10 | <10 | <10 | — | — |
| 33 | <10 | 17 | <10 | 8% | — |
| 34 | <10 | <10 | <10 | — | — |
| 35 | <10 | <10 | <10 | — | — |
| 36 | <10 | <10 | <10 | — | — |
| 37 | <10 | 10 | <10 | 6% | — |
| 38 | <10 | <10 | <10 | — | — |
| 39 | <10 | <10 | <10 | — | — |
| 40 | 89 | 68 | 52 | — | — |
| 41 | 1360 | 1100 | 1200 | — | — |
| 44 | 540 | 420 | 330 | — | — |
| 210581- 1 | <10 | <10 | <10 | — | — |
| 2 | <10 | <10 | <10 | — | — |
| 3 | <10 | <10 | <10 | — | — |
| 4 | <10 | <10 | <10 | — | — |
| 5 | <10 | <10 | <10 | — | — |
| 6 | <10 | <10 | <10 | — | — |
| 7 | <10 | <10 | <10 | — | — |
| 8 | 64 | 60 | 54 | 5% | — |
| 9 | <10 | <10 | <10 | — | — |
| 10 | 10 | 60 | 10 | 5% | — |
| 11 | 335 | 298 | 310 | — | — |
| 12 | <10 | <10 | <10 | — | — |
| 13 | <10 | <10 | <10 | — | — |
| 14 | <10 | <10 | <10 | — | — |
| 15 | <10 | <10 | <10 | — | — |
| 16 | <10 | <10 | <10 | — | — |
| 17 | <10 | <10 | <10 | — | — |
| 18 | <10 | <10 | <10 | — | — |
| 19 | <10 | <10 | <10 | — | — |
| 20 | <10 | <10 | <10 | — | — |
| 21 | 10.6 | 15 | 15 | — | — |
| 22 | <10 | 15 | <10 | — | — |
| 23 | <10 | <10 | <10 | — | — |
| 24 | <10 | 17 | 12 | 6% | 2% |
| 25 | <10 | <10 | <10 | — | — |
| 26 | <10 | <10 | <10 | — | — |
| 27 | <10 | 245 | 24 | 32% | 7% |
| 28 | <10 | 13 | <10 | — | — |
| 29 | <10 | <10 | <10 | — | — |
| 30 | <10 | <10 | <10 | — | — |
| 31 | 11 | 17 | <10 | — | — |

TABLE 1-continued

| SERUM NO. | 1 RiA | 2 PACIA | 3 PACIA + AGG. + F(AB')₂ | 4 INTERF. | 5 INTERF. |
|---|---|---|---|---|---|
| 32 | 78 | 56 | 68 | — | — |
| 33 | <10 | <10 | <10 | — | — |
| 34 | <10 | <10 | <10 | — | — |
| 35 | <10 | <10 | <10 | — | — |
| 36 | <10 | 24 | 17 | — | — |
| 37 | <10 | <10 | <10 | — | — |
| 38 | <10 | <10 | <10 | — | — |
| 39 | <10 | <10 | <10 | — | — |
| 40 | <10 | <10 | <10 | — | — |
| 41 | <10 | <10 | <10 | — | — |
| 42 | <10 | <10 | <10 | — | — |
| 290581- 1 | <10 | <10 | <10 | — | — |
| 2 | <10 | <10 | <10 | — | — |
| 3 | <10 | <10 | <10 | — | — |
| 4 | <10 | <10 | <10 | — | — |
| 5 | <10 | 12 | <10 | 9% | — |
| 6 | <10 | <10 | <10 | — | — |
| 7 | <10 | <10 | <10 | — | — |
| 8 | <10 | <10 | <10 | — | — |
| 9 | <10 | <10 | <10 | — | — |
| 10 | <10 | <10 | <10 | — | — |
| 11 | 58 | 52 | 59 | — | — |
| 12 | <10 | <10 | <10 | — | — |
| 13 | <10 | <10 | <10 | — | — |
| 14 | 128 | 170 | 190 | 7% | — |
| 15 | 225 | 140 | 170 | — | — |
| 16 | 21 | 20 | 29 | — | — |
| 17 | <10 | <10 | <10 | — | — |
| 18 | <10 | <10 | <10 | — | — |
| 19 | <10 | <10 | <10 | — | — |
| 20 | <10 | <10 | <10 | — | — |
| 21 | <10 | <10 | <10 | — | — |
| 22 | <10 | <10 | <10 | — | — |
| 23 | <10 | <10 | <10 | — | — |
| 26 | <10 | <10 | <10 | — | — |
| 27 | 327 | 310 | 300 | — | — |
| 28 | 313 | 240 | 300 | — | — |
| 29 | <10 | <10 | <10 | — | — |
| 30 | <10 | <10 | <10 | — | — |
| 31 | <10 | <10 | <10 | — | — |
| 32 | 134 | 142 | 145 | 5% | — |
| 33 | <10 | <10 | <10 | — | — |
| 34 | <10 | <10 | <10 | — | — |
| 35 | <10 | <10 | <10 | — | — |
| 36 | <10 | <10 | <10 | — | — |
| 37 | <10 | 11.5 | <10 | 7% | — |
| 38 | <10 | <10 | <10 | — | — |
| 39 | <10 | <10 | <10 | — | — |
| 40 | <10 | 13 | <10 | 8% | — |

TABLE 2

| A SAMPLE NO. | B WEEK OF PREG. | C REF VALUE (Ria) | D PACIA I | E PACIA II | F NO F(AB')₂ PACIA y | G + F(AB')₂ PACIA III | H + F(AB')₂ PACIA IV | I + F(AB')₂ PACIA y |
|---|---|---|---|---|---|---|---|---|
| 1 | 11 | <10 | 10 | 24 | 17 | <10 | <10 | <10 |
| 2 | 13 | 15 | 38 | 30 | 34 | .13 | 13 | 13 |
| 3 | 13+ | <10 | 64 | 70 | 67 | 62 | 56 | 59 |
| 4 | 14 | 32 | 42 | 50 | 46 | 27 | 27 | 27 |
| 5 | 15 | 27 | 30 | 34 | 32 | 15 | 15 | 15 |
| 6 | 15 | <10 | 18 | 18 | 18 | <10 | 10 | 10 |
| 7 | 15 | <10 | 27 | 24 | 26 | 10 | 10 | 10 |
| 8 | 15 | 13 | 38 | 38 | 38 | 10 | 12 | 11 |
| 9 | 15+ | 23 | 30 | 34 | 32 | 13 | 13 | 13 |
| 10 | 15+ | 38 | 42 | 38 | 40 | 30 | 30 | 30 |
| 11 | 15+ | 19 | 10 | 18 | 14 | 10 | 12 | 11 |
| 12 | 15+ | 17 | 18 | 24 | 21 | 10 | 10 | 10 |
| 13 | 15+ | 44 | 70 | 75 | 73 | 50 | 56 | 53 |
| 14 | 15+ | 22 | 27 | 27 | 27 | 15 | 15 | 15 |
| 15 | 15+ | 38 | 34 | 34 | 34 | 22 | 25 | 24 |
| 16 | 15+ | 21 | 24 | 27 | 26 | 12 | 12 | 12 |
| 17 | 15+ | 32 | 30 | 30 | 30 | 15 | 23 | 19 |
| 18 | 15+ | 12 | 24 | 18 | 21 | <10 | 10 | 10 |
| 19 | 15+ | 43 | 94 | 100 | 97 | 38 | 38 | 38 |
| 20 | 15+ | 30 | 30 | 34 | 32 | 15 | 23 | 19 |

TABLE 2-continued

| A SAMPLE NO. | B WEEK OF PREG. | C REF VALUE (Ria) | D PACIA I | E PACIA II | F NO F(AB')2 PACIA y | G + F(AB')2 PACIA III | H + F(AB')2 PACIA IV | I + F(AB')2 PACIA y |
|---|---|---|---|---|---|---|---|---|
| 21 | 15+ | 29 | 38 | 42 | 40 | 15 | 23 | 19 |
| 22 | 15+ | 34 | 480 | 510 | 495 | 38 | 44 | 41 |
| 23 | 16 | 21 | 50 | 46 | 48 | 15 | 19 | 17 |
| 24 | 16 | 99 | 112 | 100 | 106 | 100 | 100 | 100 |
| 26 | 16 | 32 | 48 | 40 | 44 | 28 | 25 | 27 |
| 27 | 16 | 39 | 40 | 52 | 46 | 37 | 33 | 35 |
| 28 | 16 | 20 | 36 | 36 | 36 | 20 | 28 | 24 |
| 29 | 16 | 33 | 32 | 36 | 34 | 25 | 25 | 25 |
| 30 | 16 | 40 | 32 | 32 | 32 | 33 | 37 | 35 |
| 31 | 16 | 37 | 86 | 105 | 96 | 37 | 48 | 43 |
| 32 | 16 | 38 | 48 | 65 | 56 | 28 | 28 | 28 |
| 33 | 16 | 43 | 48 | 65 | 56 | 42 | 52 | 47 |
| 34 | 16 | 21 | 29 | 40 | 35 | 28 | 20 | 24 |
| 35 | 16 | 67 | 65 | 70 | 68 | 58 | 68 | 63 |
| 36 | 16+ | 44 | 65 | 52 | 59 | 42 | 42 | 42 |
| 37 | 16+ | 33 | 48 | 76 | 62 | 25 | 28 | 27 |
| 38 | 16+ | 38 | 44 | 52 | 48 | 48 | 37 | 43 |
| 39 | 16+ | 78 | 98 | 105 | 102 | 92 | 86 | 89 |
| 40 | 16+ | 27 | 18 | 22 | 20 | 14 | 20 | 17 |
| 41 | 16+ | 13 | 22 | 29 | 26 | 17 | 13 | 15 |
| 42 | 16+ | 29 | 29 | 29 | 29 | 17 | 20 | 19 |
| 43 | 16+ | 19 | 22 | 25 | 24 | 10 | 13 | 12 |
| 44 | 16+ | 50 | 70 | 76 | 73 | 48 | 52 | 50 |
| 45 | 16+ | 39 | 40 | 48 | 44 | 33 | 28 | 31 |
| 46 | 16+ | 23 | 29 | 32 | 31 | 14 | 17 | 16 |
| 47 | 16+ | 46 | 52 | 48 | 50 | 33 | 37 | 35 |
| 48 | 16+ | 26 | 32 | 40 | 36 | 14 | 25 | 20 |
| 49 | 16+ | 39 | 52 | 60 | 56 | 33 | 33 | 33 |
| 50 | 16+ | 37 | 40 | 40 | 40 | 33 | 37 | 35 |
| 51 | 16+ | 33 | 55 | 55 | 55 | 33 | 37 | 35 |
| 52 | 16+ | 38 | 55 | 68 | 62 | 42 | 51 | 47 |
| 53 | 16+ | 29 | 37 | 37 | 37 | 26 | 33 | 30 |
| 54 | 16+ | 37 | 47 | 55 | 51 | 33 | 37 | 35 |
| 55 | 16+ | 23 | 51 | 51 | 51 | 29 | 33 | 31 |
| 56 | 16+ | 71 | 450 | 340 | 395 | 74 | 84 | 79 |
| 57 | 16+ | 40 | 37 | 47 | 42 | 29 | 33 | 31 |
| 58 | 16+ | 48 | 47 | 58 | 53 | 46 | 56 | 51 |
| 59 | 16+ | 33 | 37 | 42 | 40 | 29 | 37 | 33 |
| 60 | 16+ | 30 | 51 | 58 | 55 | 33 | 33 | 33 |
| 61 | 16+ | 20 | 30 | 37 | 34 | 19 | 26 | 23 |
| 62 | 16+ | 28 | 23 | 34 | 29 | 26 | 26 | 26 |
| 63 | 16+ | 53 | 72 | 84 | 78 | 65 | 78 | 72 |
| 64 | 16+ | 47 | 51 | 58 | 55 | 37 | 51 | 44 |
| 65 | 16+ | 24 | 26 | 34 | 30 | 26 | 26 | 26 |
| 66 | 16+ | 18 | 17 | 20 | 19 | 16 | 19 | 18 |
| 67 | 16+ | 26 | 90 | 68 | 79 | 37 | 46 | 42 |
| 68 | 16+ | 38 | 68 | 78 | 73 | 42 | 46 | 44 |
| 69 | 16+ | 26 | 34 | 37 | 36 | 26 | 29 | 28 |
| 70 | 16+ | 34 | 34 | 42 | 38 | 29 | 33 | 31 |
| 71 | 16+ | 21 | 23 | 26 | 25 | 22 | 22 | 22 |
| 72 | 16+ | 28 | 30 | 37 | 34 | 29 | 33 | 31 |
| 73 | 16+ | 297 | 520 | 500 | 510 | 400 | 400 | 400 |
| 74 | 16+ | 50 | 68 | 68 | 68 | 56 | 51 | 54 |
| 75 | 16+ | 27 | 37 | 42 | 40 | 33 | 37 | 35 |
| 76 | 16+ | 30 | 800 | 940 | 820 | 22 | 26 | 24 |
| 77 | 16+ | 37 | 63 | 68 | 66 | 40 | 40 | 40 |
| 78 | 16+ | 36 | 41 | 33 | 37 | 32 | 36 | 34 |
| 79 | 16+ | 59 | 68 | 72 | 70 | 51 | 57 | 54 |
| 80 | 16+ | 163 | 165 | 175 | 170 | 142 | 148 | 145 |
| 81 | 16+ | 35 | 33 | 41 | 37 | 32 | 32 | 32 |
| 82 | 16+ | 31 | 33 | 28 | 31 | 20 | 20 | 20 |
| 83 | 16+ | 43 | 45 | 50 | 48 | 36 | 29 | 33 |
| 84 | 16+ | 35 | 45 | 45 | 45 | 36 | 32 | 34 |
| 85 | 16+ | 41 | 45 | 37 | 41 | 36 | 40 | 38 |
| 86 | 16+ | 46 | 59 | 63 | 61 | 40 | 40 | 40 |
| 87 | 16+ | 35 | 72 | 68 | 70 | 32 | 40 | 36 |
| 88 | 16+ | 34 | 37 | 37 | 37 | 26 | 29 | 28 |
| 89 | 16+ | 40 | 59 | 63 | 61 | 50 | 54 | 52 |
| 90 | 16+ | 36 | 255 | 255 | 255 | 135 | 148 | 142 |
| 91 | 16+ | 40 | 135 | 160 | 148 | 148 | 148 | 148 |
| 92 | 16+ | 35 | 45 | 50 | 48 | 40 | 36 | 38 |
| 93 | 16+ | 27 | 22 | 22 | 22 | 22 | 22 | 22 |
| 94 | 16+ | 11 | 19 | 15 | 17 | 14 | 20 | 17 |
| 95 | 16+ | 23 | 22 | 22 | 22 | 22 | 22 | 22 |
| 96 | 17+ | 24 | 19 | 22 | 21 | 22 | 20 | 21 |
| 97 | 17+ | 33 | 68 | 59 | 64 | 62 | 54 | 58 |
| 98 | 17+ | 36 | 45 | 45 | 45 | 36 | 36 | 36 |

TABLE 2-continued

| A SAMPLE NO. | B WEEK OF PREG. | C REF VALUE (Ria) | D PACIA I | E PACIA II | F NO F(AB')2 PACIA y | G + F(AB')2 PACIA III | H + F(AB')2 PACIA IV | I + F(AB')2 PACIA y |
|---|---|---|---|---|---|---|---|---|
| 99 | 17+ | 24 | 68 | 59 | 64 | 26 | 26 | 26 |
| 100 | 17+ | 16 | 50 | 54 | 52 | 40 | 32 | 36 |

We claim:

1. A rear wheel steer angle control system for a vehicle, comprising;
   (a) actuating means for steering rear wheels of the vehicle in response to a control signal;
   (b) means for sensing a steering wheel angle of the vehicle;
   (c) means for sensing a vehicle speed of the vehicle; and
   (d) controlling means connected with said steering wheel angle sensing means and said vehicle speed sensing means for controlling a rear wheel steer angle $\delta_r[(s)]$ with respect to a front wheel steer angle $\delta_f[(s)]$ by producing a control signal representing said rear wheel steer angle in accordance with a mathematical relationship expressed as;

$$\frac{\delta_r(s)}{\delta_f(s)} = \frac{K + T1 \cdot s}{1 + T2 \cdot s}$$

where $\delta_r(s)$ is the Laplace transform of said rear wheel steer angle $\delta_r$,
$\delta_f(s)$ is the Laplace transform of said front wheel steer angle $\delta_f$,
s is a complex variable,
K, T1, and T2 and first, second and third control parameters given by;

$$K = \frac{C_1 \{aMV^2 + C_2 l_0(l_3 - b)\}}{C_2 \{bMV^2 + C_1 l_0(l_3 + a)\}}$$

$$T1 = \frac{C_1 V(aMl_3 - I)}{C_2 \{bMV^2 + C_1 l_0(l_3 + a)\}}$$

$$T2 = \frac{V(bMl_3 + I)}{bMV^2 + C_1 l_0(l_3 + a)}$$

M is a constant representing a vehicle mass,
I is a constant representing a yawing moment of inertia,
$l_0$ is a constant representing a wheelbase,
a is a constant representing a first distance between a center of gravity of the vehicle and a front wheel position,
b is a constant representing a second distance between said center of gravity and a rear wheel position,
$l_3$ is a third distance which is a quantity representing a distance between said center of gravity and a zero sideslip angle position at which a vehicle sideslip angle is zero, and which is positive when said zero sideslip angle position is closer to said rear wheel position than said center of gravity,
$C_1$ is a constant representing a front wheel cornering power,
$C_2$ is a constant representing a rear wheel cornering power, and
V is said vehicle speed.

2. A method according to claim 1, wherein said fragments of said second immunoglobulin are F(ab')2 fragments.

3. A method according to claim 2, wherein said F(ab')2 fragments of said second immunoglobulin are aggregated.

4. A method according to claim 1, wherein said fragments of second immunoglobulin are chemically aggregated.

5. A method according to claim 1, wherein said fragments of said second immunoglobulin are coupled to a solid insoluble support or to a soluble carrier.

6. A method according to claim 1, wherein step (a) finely divided particles having said fragments of said first immunoglobulin coated thereon are included in the reaction mixture, the particles being agglutinatable in dependence on the amount of analyte in the mixture, and in step (c) the amount of analyte is determined by counting unagglutinated particles; and wherein said fragments of said second immunoglobulin are present in solution in the reaction mixture during the assay.

7. A method according to claim 1, wherein said fragments of said first immunoglobulin are F(ab')2 fragments of IgG.

8. A method of immunoassay of an analyte in human serum which comprises:
   (a) forming a reaction mixture of
      (i) the human serum; and
      (ii) finely divided particles bearing F(ab')2 fragments of a first immunoglobulin from a non-human animal, the reaction mixture being free from whole first immunoglobulin and from F(c) fragments thereof, the first immunoglobulin being immunospecific to the analyte in the reaction mixture; and
      (iii) F(ab')2 fragments of a second immunoglobulin from said non-human animal, said F(ab')2 fragments of said second immunoglobulin being non-reactive with said analyte but reactive with human antibodies to said (Fab')2 fragments of said first immunoglobulin from said non-human animal, and
   (b) assaying the amount of analyte present by counting unagglutinated particles and comparing counts observed with counts observed for a series of standard composition containing known concentrations of said analyte.

* * * * *

UNITED STATES PATENT AND TRADEMARK OFFICE
CERTIFICATE OF CORRECTION

PATENT NO. : 4,946,796
DATED : August 7, 1990
INVENTOR(S) : Daniel Collet-Cassart, et al.

It is certified that error appears in the above-identified patent and that said Letters Patent is hereby corrected as shown below:

Column 13, lines 12-64, and Column 14, lines 10-16, delete Claim 1 in its entirety and substitute therefor the following:

1. In a method of immunoassay of an analyte in a biological fluid from a first animal species, comprising forming a reaction mixture between said biological fluid and antigen-binding fragments of a first immunoglobulin from a second animal species, which is immunologically specific to said analyte in the reaction mixture, the reaction mixture being free from whole said first immunoglobulin and F(c) fragments thereof, the improvement comprising reducing interference in the immunoassay from a reaction between said antigen-binding fragments of said first immunoglobulin and any antibodies from the first animal species reactive therewith which are present in the biological fluid, by the steps of:

(a) also mixing the biological fluid with antigen-binding fragments of a second immunoglobulin from said second animal species, which antigen-binding fragments of said second immunoglobulin do not bind to said analyte but do bind to said antibodies from said first animal species;

(b) thereby reducing said interference; and (c) thereafter analyzing the reaction mixture for complexes formed by said antigen-binding fragments of said first immunoglobulin and said analyte.

Column 14, line 29, before "step" insert -- in -- .

UNITED STATES PATENT AND TRADEMARK OFFICE
CERTIFICATE OF CORRECTION

PATENT NO. : 4,946,796  
DATED : August 7, 1990  
INVENTOR(S) : Daniel Collet-Cassart, et al.

Page 2 of 2

It is certified that error appears in the above-identified patent and that said Letters Patent is hereby corrected as shown below:

(b) thereby reducing said interference; and (c) thereafter analyzing the reaction mixture for complexes formed by said antigen-binding fragments of said first immunoglobulin and said analyte.

Column 14, line 29, before "step" insert -- in -- .

Signed and Sealed this

Eighteenth Day of February, 1992

Attest:

HARRY F. MANBECK, JR.

*Attesting Officer*  *Commissioner of Patents and Trademarks*